US008426357B2

(12) United States Patent
Kraehmer et al.

(10) Patent No.: US 8,426,357 B2
(45) Date of Patent: Apr. 23, 2013

(54) MULTIMERIC CONJUGATE

(75) Inventors: Ralf Kraehmer, Panketal (DE); Frank Leenders, Berlin (DE); Erik Fiedler, Halle (DE); Thomas Hey, Bad Nauheim (DE); Ulrike Fiedler, Halle (DE); Markus Fiedler, Halle (DE)

(73) Assignees: celares GmbH, Berlin (DE); Scil Proteins GmbH, Halle (DE)

( * ) Notice: Subject to any disclaimer, the term of this patent is extended or adjusted under 35 U.S.C. 154(b) by 321 days.

(21) Appl. No.: 12/525,902

(22) PCT Filed: Feb. 11, 2008

(86) PCT No.: PCT/EP2008/051598
§ 371 (c)(1),
(2), (4) Date: Sep. 28, 2009

(87) PCT Pub. No.: WO2008/096012
PCT Pub. Date: Aug. 14, 2008

(65) Prior Publication Data
US 2010/0143387 A1    Jun. 10, 2010

(30) Foreign Application Priority Data
Feb. 9, 2007 (EP) .................... 07002848

(51) Int. Cl.
| A61K 38/18 | (2006.01) |
|---|---|
| A61K 38/00 | (2006.01) |
| A61K 39/11 | (2006.01) |
| A61K 35/00 | (2006.01) |
| A61K 47/30 | (2006.01) |
| C08G 63/00 | (2006.01) |
| C08G 71/00 | (2006.01) |
| C08G 69/00 | (2006.01) |
| C08G 75/00 | (2006.01) |
| C08G 73/00 | (2006.01) |
| C07K 17/02 | (2006.01) |
| C07K 17/08 | (2006.01) |

(52) U.S. Cl.
USPC ........... 514/1.1; 514/18.9; 514/13.3; 514/8.1; 514/9.6; 528/271; 528/374; 528/396; 528/422; 528/425; 525/54.1; 530/399

(58) Field of Classification Search ............... 514/1.1, 514/18, 13.3, 8.1, 9.69; 528/271, 374, 396, 528/422, 425; 525/54.1; 530/399
See application file for complete search history.

(56) References Cited

U.S. PATENT DOCUMENTS
2005/0175620 A1* 8/2005 Jones ........................ 424/178.1
2006/0182714 A1* 8/2006 Behrens et al. .............. 424/85.2

FOREIGN PATENT DOCUMENTS
| WO | WO 95/25763 | 9/1995 |
|---|---|---|
| WO | WO 01/62827 | 8/2001 |
| WO | WO 03/033028 | * 4/2003 |
| WO | WO 03/033028 A2 | * 4/2003 |
| WO | WO 03/093346 | 11/2003 |
| WO | WO 2004/106368 | 12/2004 |
| WO | WO 2006/040129 | * 4/2006 |

OTHER PUBLICATIONS

Fiedler et al. (WO 2006/040129 Published Apr. 20, 2006—English Translation).*
Zhao (FEBS Letters, 563, pp. 241-245, published 2004).*
Albrecht et al., "Monospecific bivalent scFv-Sh: Effects of linker length and location of an engineered cysteine on production, antigen binding activity and free SH accessibility," Journal of Immunological Methods, . Elsevier Science Publishers B.V.,Amsterdam, NL, vol. 310, No. 1-2, pp. 100-116 (Mar. 20, 2006) XP005334493.
Albrecht et al., "Production of Soluble ScFvs with C-Terminal-Free Thiol for Site-Specific Conjugation or Stable Dimeric ScFvs on Demand," Bioconjugate Chemistry, vol. 15, pp. 16-26 (2004) XP002458164.
Berna et al., "Novel Monodisperse PEG-Dendrons as New Tools for Targeted Drug Delivery: Synthesis, Characterization and Cellular Uptake," Biomacromolecules, vol. 7, pp. 146-153 (2006) XP002458162.
Chapman, A., "Pegylated Antibodies and Antibody Fragments for Improved Therapy: A Review," Advanced Drug Delivery Reviews, Amsterdam, NL, vol. 54, No. 4, pp. 531-545 (Jun. 17, 2002) XP001199533.
Galande et al., "Enzyme-Targeted Fluorescent Imaging Probes on a Multiple Antigenic Peptide Corem" J. Med. Chem, vol. 49, pp. 4715-4720 (2006) XP002458161.
Notification Concerning Transmittal of International Preliminary Report on Patentability corresponding to International Application No. PCT/EP2008/0151598 dated Aug. 20, 2009.
Notification Concerning Transmittal of International Search Report and the Written Opinion of the International Searching Authority, or the Declaration corresponding to International Application No. PCT/EP2008/0151598 dated Jun. 19, 2009.
Yang et al., "In vitro enzymatic stability of dendritic peptides," Journal of Biomedical Materials Research, Wiley, New York, NY, US, vol. 76, No. 2, pp. 398-407 (2006) XP008085738.
Yang et al., "Penicillin V-conjugated PEG-PAMAM star polymers," Journal of Biomaterials Science, vol. 14, No. 10, pp. 1043-1056 (2003) XP008085754.
Zhang et al., "Multiple-Peptide Conjugates for. Binding B-Amyloid Plaques of Alzheimer's Disease," Bioconjugate Chemistry, vol. 14, pp. 86-92 (2003) XP002458160.

* cited by examiner

Primary Examiner — Richard Schnizer
Assistant Examiner — Alma Pipic
(74) Attorney, Agent, or Firm — Jenkins, Wilson, Taylor & Hunt, P.A.

(57) ABSTRACT

The present invention is directed to a multimeric agent and a multimeric conjugate formed from this multimeric agent and a biologically active agent. Said multimeric conjugates have a longer life time in vivo and an increased avidity compared to the unmodified biologically agent. The present invention is further directed to a pharmaceutical or diagnostic composition containing said conjugate as well as to a method of its production. The invention additionally provides the use of said conjugates for the detection, determination, separation and/or isolation of a specific binding partner and for the diagnosis, prophylaxis and treatment of diseases in which the specific binding partner is directly or indirectly involved.

25 Claims, 5 Drawing Sheets

A

B

SEQUENCE LISTING

<160> NUMBER OF SEQ ID NOS: 9

<210> SEQ ID NO 1
<211> LENGTH: 65
<212> TYPE: DNA
<213> ORGANISM: Artificial sequence
<220> FEATURE:
<223> OTHER INFORMATION: Artificially synthesized F1 primer

<400> SEQUENCE: 1
ggagaccaca acggtttccc tctagaaata attttgttta actttaagaa ggagatatac    60
atatg                                                                65

<210> SEQ ID NO 2
<211> LENGTH: 48
<212> TYPE: DNA
<213> ORGANISM: Artificial sequence
<220> FEATURE:
<223> OTHER INFORMATION: Artificially synthesized SPWS57Crev primer

<400> SEQUENCE: 2
cacaaagagt gcggccatct tccagttgct tgcctgccca gatgagcc                 48

<210> SEQ ID NO 3
<211> LENGTH: 34
<212> TYPE: DNA
<213> ORGANISM: Artificial sequence
<220> FEATURE:
<223> OTHER INFORMATION: Artifically synthesized SPWS57Cfw primer

<400> SEQUENCE: 3
ggaagatggc cgcactcttt gtgactacaa catc                                34

<210> SEQ ID NO 4
<211> LENGTH: 22
<212> TYPE: DNA
<213> ORGANISM: Artificial sequence
<220> FEATURE:
<223> OTHER INFORMATION: Artificially synthesized pET20b+rev_help primer

<400> SEQUENCE: 4
gggaagaaag cgaaaggagc gg                                             22

<210> SEQ ID NO 5
<211> LENGTH: 61
<212> TYPE: DNA
<213> ORGANISM: Artificial sequence
<220> FEATURE:
<223> OTHER INFORMATION: Artificially synthesized WUBIFlagXhoIrev primer

<400> SEQUENCE: 5
ccattccacc tcgagaccct tatcatcatc atctttgtaa tcgccgccac gcagacgcag    60
c                                                                    61

<210> SEQ ID NO 6
<211> LENGTH: 285
<212> TYPE: DNA
<213> ORGANISM: Artificial sequence
<220> FEATURE:
<223> OTHER INFORMATION: Artificially synthesized 8A7 (S57C) DNA
       Sequence

```
<400> SEQUENCE: 6
atgcggatct tgtgggttac cctgaccggc aagaccatca ctctggaggt ggagcccagt    60
gacaccatcg aaaatgtgaa ggccaagatc aagataaag aaggcattcc ccccgaccag   120
cagaggctca tctgggcagg caagcaacta gaagatggcc gcactctttg tgactacaac   180
atcctgaaga ctggtcctct gcacctggtc ctccgcctga ggggcggcga ttacaaagat   240
gatgatgata aggtctcga gcaccaccac caccaccact gataa                    285

<210> SEQ ID NO 7
<211> LENGTH: 93
<212> TYPE: PRT
<213> ORGANISM: Artificial sequence
<220> FEATURE:
<223> OTHER INFORMATION: Artificially synthesized 8A7 (S57C) amino acid
      sequence

<400> SEQUENCE: 7

Met Arg Ile Phe Val Val Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Cys Asp Tyr Asn Ile Leu Lys Thr
    50                  55                  60

Gly Pro Leu His Leu Val Leu Arg Leu Arg Gly Gly Asp Tyr Lys Asp
65                  70                  75                  80

Asp Asp Asp Lys Gly Leu Glu His His His His His His
                85                  90

<210> SEQ ID NO 8
<211> LENGTH: 285
<212> TYPE: DNA
<213> ORGANISM: Artificial sequence
<220> FEATURE:
<223> OTHER INFORMATION: Artificially synthesized Ubiquitin (S57C) DNA
      sequence

<400> SEQUENCE: 8
atgcagatct tcgtgaagac cctgaccggc aagaccatca ctctggaggt ggagcccagt    60
gacaccatcg aaaatgtgaa ggccaagatc aagataaag aaggcattcc ccccgaccag   120
cagaggctca tctgggcagg caagcaactg gaagatggcc gcactctttg tgactacaac   180
atccagaaag agtcgaccct gcacctggtc ctccgcctga ggggcggcga ttacaaagat   240
gatgatgata aggtctcga gcaccaccac caccaccact gataa                    285

<210> SEQ ID NO 9
<211> LENGTH: 93
<212> TYPE: PRT
<213> ORGANISM: Artificial sequence
<220> FEATURE:
<223> OTHER INFORMATION: Artificially synthesized Ubiquitin (S57C)
      amino acid sequence

<400> SEQUENCE: 9

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30
```

```
Lys Glu Gly Ile Pro Pro Asp Gln Gln Arg Leu Ile Trp Ala Gly Lys
        35              40                  45

Gln Leu Glu Asp Gly Arg Thr Leu Cys Asp Tyr Asn Ile Gln Lys Glu
    50              55                  60

Ser Thr Leu His Leu Val Leu Arg Leu Arg Gly Gly Asp Tyr Lys Asp
65              70                  75                  80

Asp Asp Asp Lys Gly Leu Glu His His His His His His
            85              90
```

MULTIMERIC CONJUGATE

Figure 1:
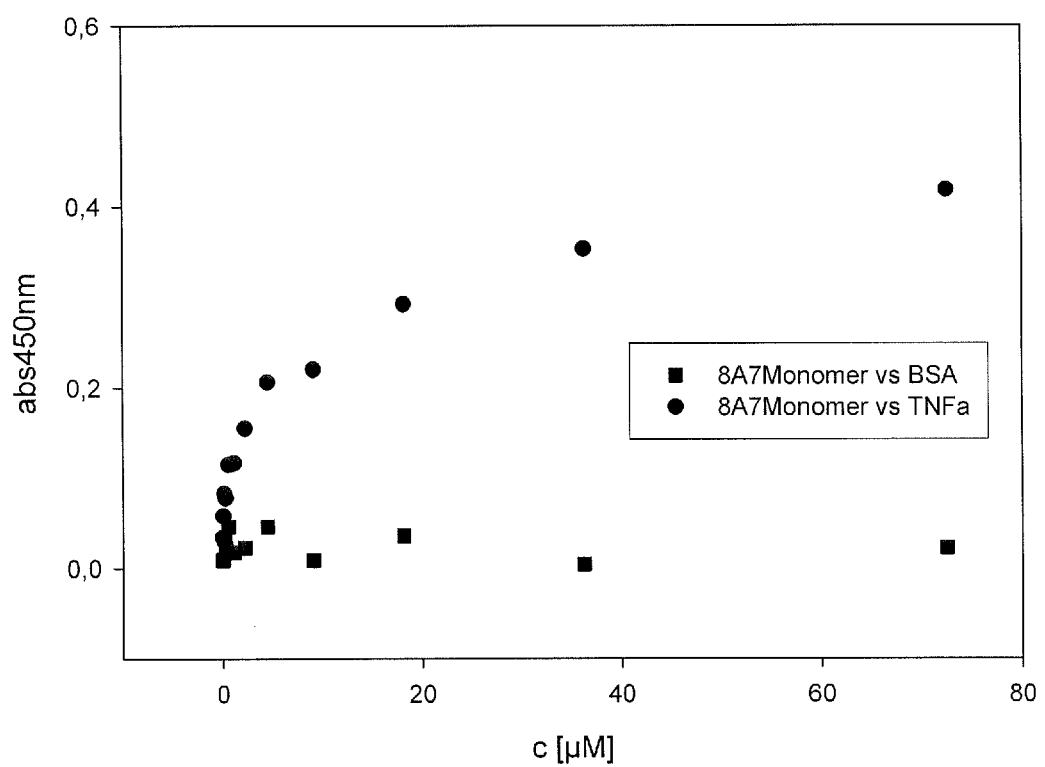

The present invention is directed to a multimeric agent and a multimeric conjugate formed from this multimeric agent and a biologically active agent. Said multimeric conjugates have longer life time in vivo and an increased avidity compared to the unmodified biologically agent. The present invention is further directed to a pharmaceutical or diagnostic composition containing said conjugate as well as to a method of its production. The invention additionally provides the use of said conjugates for the detection, determination, separation and/or isolation of a specific binding partner and for the diagnosis, prophylaxis and treatment of diseases in which the specific binding partner is directly or indirectly involved.

BACKGROUND OF THE INVENTION

The development of biopharmaceuticals as medical substances or as biotechnological products for applications in industry and science has made rapid progress during the past decades. Numerous biologically active agents selected from the classes of peptides, proteins, nucleic acids or small molecules have been identified, developed, or already been marketed.

Of major commercial interest for the development of therapeutics have been growth factors and their receptors like TNF, VEGF, or EGF. Furthermore, biologically active agents with antigen binding activity like antibodies, antibody fragments, antibody like molecules, and scaffold proteins have gained significant relevance.

The production of polyclonal antibodies is commonly known. Detailed protocols can be found for example in Green et al., Production of Polyclonal Antisera, in *Immunochemical Protocols* (Manson, editor), pages 1-5 (Humana Press 1992) and Coligan et al., Production of Polyclonal Antisera in Rabbits, Rats, Mice and Hamsters, in *Current Protocols In Immunology*, section 2.4.1 (1992). In addition, several techniques regarding the purification and concentration of polyclonal antibodies, as well as of monoclonal antibodies, are well known (Coligan et al., Unit 9, *Current Protocols in Immunology*, Wiley Interscience, 1994).

The production of monoclonal antibodies is commonly known as well. Examples include the hybridoma method (Kohler and Milstein, 1975, Nature, 256:495-497, Coligan et al., section 2.5.1-2.6.7; and Harlow et al., *Antibodies: A Laboratory Manual, page* 726 (Cold Spring Harbor Pub. 1988)), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96).

Despite the achievements and possibilities provided by antibodies certain disadvantages can limit the practical use. Thus, it is a problem to provide them in sufficient amounts. The production of functional antibodies is carried out in eukaryotic cell culture systems—an extraordinarily cost-intensive method. Furthermore, the low tissue penetration of the antibody molecules due to their large size and their long residence time in the serum (slow blood clearance), respectively, hamper many therapeutic applications. Although smaller fragments of antibodies such as scFv or Fab fragments (see above) can be prepared in bacteria and thus basically at lower costs, the yields of this recombinant production, however, are lower than the desired level due to their unfavourable folding properties and the required formation of several disulfide bonds. Moreover, recombinant antibody fragments often are less stable and show a lower binding activity as compared to the parental antibodies.

In order to circumvent such limitations attempts have been made to impart the principle of antibody binding—namely the binding by means of a hypervariable surface-exposed region localized on a conserved protein scaffold—to other proteins (Skerra, 2000). This means that essentially variable loops are varied in order to generate an artificial binding property. For this purpose, usually natural binding proteins such as lipocalins (Beste et al., 1999) or the fibronectin type III domain (Koide et al., 1998) have been used as a starting point for which binding sites are formed in a manner analogously to antibodies from flexible "loop" structures whose modification enables the recognition of ligands different from the natural ones.

Beside DNA-derived binding molecules, so called aptamers, a further alternative to antibodies may be binding molecules selected from the group consisting of proteins of the protein superfamily of "ubiquitin-like proteins", in particular those having an ubiquitin-like folding motif as well as fragments or fusion proteins thereof each having the ubiquitin-like folding motif. WO 2004/106368 relates to modified proteins of this superfamily of "ubiquitin-like proteins", proteins that have an ubiquitin-like fold. As a result of said modification, the proteins have a binding affinity with respect to a predetermined binding partner that did not exist previously. The contents of WO 2004/106368 are also incorporated herein by reference.

For scaffold derived binding molecules it is valid that the binding protein due to modifications of those amino acids forming a contiguous region on the surface of the protein, in at least one surface-exposed region of the protein preferably has a binding affinity with respect to a predetermined binding partner that did not exist previously while the original folding motif is maintained.

In summary, it turned out that a possible alternative to antibodies or aptamers thus is a group of proteins having antibody like binding behaviour.

However, there still remain major limitations for the therapeutic use of antibodies, antibody fragments, and antibody like molecules such as scaffold proteins either because of their rapid renal excretion, or poor solubility, or immunogenicity, or reduced binding affinity and/or avidity as compared with native human antibodies.

For this reason, many attempts have been made to improve the pharmacological properties of such antigen binding proteins routinely having molecular weights far below 50,000 Dalton (Da). Reviews have been published in Nature Biotechnology Volume 21, Number 4, 2006: 1126-36 or Nature Reviews Immunology, Vol 6, 2006: 343-357.

PEGylation, the covalent attachment of polyethylene glycol (PEG) to a biologically active agent, has been applied to numerous proteins and antibody fragments in order to reduce their immunogenicity and increase their circulation time in plasma (*CANCER BIOTHERAPY & RADIOPHARMACEUTICALS*, Volume 21, Number 4, 2006: 285-304). However, in many cases PEGylation leads to reduced target association rates via a dual blocking mechanism (*Mol Pharmacol*, Volume 68, 2005: 1439-1454). Chapman, A P gives a detailed overview about the divergent effects of a PEGylation for various antibodies or antibody fragments (*Advanced Drug Delivery Reviews*, Volume 54, 2002: 531-545).

A further approach to increase half-life and avidity of antibody like fragments has been the multimerization of two or more of such agents by introducing inter molecular disulfide bridges, peptide linkers or chemical cross-linkers. Improved tumor targeting with chemically cross-linked recombinant antibody fragments has been demonstrated for di- and trimeric Fab fragments as compared with the monomeric Fab. However, the half-life of Fab fragments could not be improved by this method (Cancer Res. (1994); 54 (23): 6176-85).

Both multimerization and PEGylation represent useful strategies to tailor the pharmacokinetic properties of therapeutic antibodies and their combined use can additively improve tumor targeting (JOURNAL OF BIOLOGICAL CHEMISTRY VOL. 281, NO. 46, pp. 35186-35201, Nov. 17, 2006). However, the process of subsequently cross-linking and PEGylating an antigen binding agent is complex and thus bears certain disadvantageous with regard to yield and costs.

Consequently, attempts have been made to combine multimerization and PEGylation in one multimeric agent. In this regard, several approaches have been published.

US 2003/0211078 is related to novel pharmaceutically useful compositions that bind to a biological molecule, having improved circulatory half-life, increased avidity, increased affinity, or multifunctionality, and methods of use thereof. A pseudo-antibody is disclosed comprising an organic moiety covalently coupled to at least two target-binding moieties, wherein the target-binding moieties are selected from the group consisting of a protein, a peptide, a peptidomimetic, and a non-peptide molecule that binds to a specific targeted biological molecule. An example of such a pseudo-antibody construct shows a multimeric structure having several target binding molecules, which are linked by one single PEG moiety.

WO 03/093346 relates to high molecular weight multifunctional polyethylene glycol derivatives having a complex branched structure. From synthesis schemes 1 and 2 as well as claim 1 of WO 03/093346, it is obvious that the core structure of such a molecule results from reacting an activated PEG with a hetero-tri-functional molecule such as 2-amino-1,3-propanediol or 1,3-Diamino-2-propanol. In this way the use of such multifunctional polyethylene glycol derivatives is limited.

From US 2005/0175620 so called valency platform molecules are known comprising high molecular weight polyethylene glycol moieties, as well as conjugates thereof with biologically active molecules, and methods for their preparation. The high molecular weight polyethylene glycol moiety has, for example, a molecular weight of greater than 22,000 Daltons, for example at least 40,000 Daltons. In one embodiment, a composition comprising the valency platform molecules is provided, wherein the molecules have a polydispersity less than about 1.2. Conjugates of the valency platform molecule and a biologically active molecule, such as a saccharide, polysaccharide, amino acid, poly(amino acid), nucleic acid or lipid also are provided. Thus, this citation only describes high-molecular PEG reagents useful for prolonging half-life of comparably low molecular weight biologically active agents. However, such high-molecular PEG reagents are not suitable to increase the avidity of biologically active binding molecules, such as antibodies or antibody like proteins.

WO 2005/061005 describes branched molecular scaffolds which are capable of linking two polymer residues (derived, for example, from polyethylene glycol) to two, three or four residues derived from biologically active molecules (e.g., from whole antibodies or from functionally active fragments or derivatives thereof), the latter being attached to the scaffold by means of hydrolytically stable linkages.

WO 03049684 provides a pseudo-antibody comprising an organic moiety covalently coupled to at least two target-binding moieties, wherein the target-binding moieties are selected from the group consisting of a protein, a peptide, a peptidomimetic, and a non-peptide molecule that binds to a specific targeted biological molecule. The pseudo-antibody may affect a specific ligand in vitro, in situ and/or in vivo.

Some multimeric agents have been published using amino acids such as lysine residues as branching unit. Galande, A. K. et al. prepared multimeric imaging probes using the multiple antigenic peptide (MAP) system as the core branching unit (*J. Med. Chem.*, Vol. 49, 2006: 4715-4720). The application of such multimeric agents is limited to special applications. Berna, M. et al. prepared monodisperse PEG-Dendrons by reacting multiple lysine residues with PEG (*Biomacromolecules*, Vol. 7, No. 1, 2006: 146-153). However, with increasing number of lysine residues the number of peptide bonds increases. These peptide bonds may be susceptible to hydrolysis by peptidases and furthermore to recognition by the immune system resulting in undesired side effects. Furthermore, amino acids and peptides are routinely prepared by involving microbial production processes. Thus, those basic materials bear the risk of contaminations with microbial substances such as toxins.

A multimeric agent based on PEGylated polyamidoamine (PAMAM) has been published by Yang, H. and Lopina, S. T. (*J. Biomed. Mat. Res. A*, Vol. 76, No. 2, 2006:398-407). PAMAM routinely bears more than 30 free amino groups and consequently is only useful for the multimerization of large numbers of biologically active molecules. Furthermore, it will hardly be possible to obtain a uniform quality with a defined number of attaching sites for a biologically active molecule based on PAMAM.

Numerous multimeric homofunctional PEG molecules have been published basing on polyalcohols as the central core unit such as glycerol or pentaerythritol. Such multimeric homofunctional PEG molecules are prepared either by Williamson ether synthesis or by ethoxylation of the hydroxyl groups of the central unit. Both synthesis strategies result in ether bonds between PEG and the central branching moiety. Related patents are cited in the following:

WO 03/033028 claims a molecule comprising a non-protein polymer, e.g. PEG, having at least three proteins linked thereto. The structure of the central non-protein polymer is based on a polyglycerol (Shearwater Polymers Inc.) as disclosed in example 1. For structural details of the non-protein polymer we refer to WO 01/62827.

WO 01/62827 of Shearwater Corporation discloses homofunctional multimeric non-peptidic polymers directly bonded to the nitrogen of an N-maleimidyl moiety. The branching unit is selected from the group consisting of glycerol, glycerol oligomers, pentaerythritol, sorbitol, and lysine. The latter is only suitable for the preparation of bi- or trivalent multimeric agents. All other branching units require the above mentioned reactions and end in an ether bond as illustrated in example 4 of WO 01/62827 for the preparation of 4-arm 10 KDa PEG maleimide.

WO 95/25763 discloses dendrimeric-type macromolecules prepared by Williamson ether synthesis with Pentaerythritol as central branching unit. Yields of such a synthesis are comparably low making this approach less attractive for commercial applications. Stein et al. published the preparation of multiple-peptide conjugates by using an eight arm branched amino-PEG from Shearwater polymers (*Bioconjugate Chem.* Vol 14, No. 1, 2003: 86-92). The latter is prepared by ethoxylation of a polyglycerol (for details see shearwater product catalogue, furthermore we refer to WO 01/62827)).

The before cited publications on multimeric agents based on polyalcohols all bear significant structurally determined disadvantages:

a) A Williamson ether synthesis results in essentially uniform multimeric agents, however, yield of such a reaction is very low and makes this approach unattractive for commercial applications.

b) Ethoxylation results in high yields of the final product, however, due to the polymerisation process the resulting multimeric agents routinely show unfavourable high variations in quality and furthermore are not available with defined low molecular weights.

Despite the above-mentioned achievements, multimerization of four biologically binding molecules, in theory, can be achieved by using tetra-functionalized PEG, it is not a practical option since homogeneous tetra-functionalized PEG suitable for pharmaceutical use are not readily available (J. Immunol. Methods 2006 Vol 310 (1-2): 100-16).

In summary, there is still a great demand for multimeric agents with four or more attachment sites, which have uniform quality, variable linker length, and a defined number of reactive groups, and furthermore are capable of increasing the solubility, modulating the molecular weight, and improving the avidity of conjugates with biologically active molecules thereof.

SUMMARY OF THE INVENTION

Therefore, it is an object of the invention to provide a multimeric binding agent and a multimeric conjugate obtained therefrom having improved in vivo properties as for example, reduced renal elimination, and which brings about a reduced dosage of a said conjugate in vivo compared to monomeric binding molecules. It is a further object of the present invention to provide a multimeric binding agent comprising conjugate showing a higher avidity compared to the avidity of the monomeric binding molecule. Furthermore, it is an object to provide methods of producing those agents and constructs as well as the use of the latter in in vitro applications, e.g., determination, separation and/or isolation of a corresponding binding partner, or in in vivo applications, e.g., in the diagnosis, prophylaxis and treatment of diseases in which the corresponding binding partner is directly or indirectly involved.

These objects are achieved by the subject-matter of the independent claims. Preferred embodiments are set forth in the dependent claims.

There is an increasing demand for well-defined, multivalent polymer reagents, which are capable of multimerizing active agents, in particular biologically active agents. The present invention meets that demand.

According to the present invention, it surprisingly turned out that already relatively short polymer chains, used in such a multimeric agent, may bring about a substantial increase in avidity. Thus, the multimeric conjugate of the present invention surprisingly showed a dramatically increased binding avidity for corresponding binding partners. As an example, a tetrameric conjugate (comprising a tetramerized PEGylated binding molecule) resulted in at least more than 30 fold increase of the avidity effect compared to the monomeric PEGylated binding molecule. Furthermore, it surprisingly turned out that already small synthetic starting material could be used to prepare multimeric agents according to the present invention in a very efficient convergent synthesis.

As a summary, the present conjugate is showing unexpected and improved binding characteristics which can be exploited for in vivo and in vitro applications.

DETAILED DESCRIPTION OF THE INVENTION

According to a first aspect, the present invention provides a multimeric agent of the following formula:

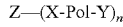

wherein

Z is a homo-multifunctional hydrocarbon, preferably branched, with 1 to 50 carbon atoms which optionally contains heteroatoms;

X is a hydrocarbon linker with 1-15, preferably 2-10, more preferably 3-5 carbon atoms, which optionally contains heteroatoms and which is capable of forming a stable linkage between Z and Pol;

Pol is a water soluble, non-toxic polymer;

Y is a coupling agent capable of coupling to a biologically active agent, and n is an integer from 4-20, preferably 4-15, more preferably 4-8.

Z preferably is selected from oligoamines, oligocarboxylic acids, oligothiols, oligoalkenes, oligoalkynes, oligohydrazines, and oligoazides.

It is noted that Z preferably is not selected from natural compounds, such as peptidic and amino acid compounds. It turned out that by using those compounds, impurities are introduced into the reaction mixture leading to undesired effects. In practical use this can mean a reduced product yield, variations in quality, and contamination with microbial toxins. Consequently, Z is preferably prepared by synthesis from chemically pure synthetic starting material and, as such, is a synthetic material.

In further preferred embodiments Z is non-chiral. It turned out that by using those compounds, conjugates of the multimeric agent can form diastereoisomers with drugs that are chiral. This is of special relevance if the drug has a low molecular weight. Such diastereoisomers have different physicochemical properties and often show different pharmacologic properties with regard to their activity in vivo. Consequently, diastereoisomers are highly undesired in pharmaceutical preparations.

It is noted that these groups of compounds correspond to the starting materials used for Z in the synthesis of the multimeric agent and do not necessarily reflect the exact chemical structure of Z in the final compound of Z—(X-Pol-Y)$_n$. For example, if Z is an oligoamine, X may be for example an amide-linker (as defined below) in the finally synthesized structure Z—(X-Pol-Y)$_n$.

In particular preferred are oligoamines, such as: ethylenediamine, diethylenetriamine, triethylenetetramine, pentaethylenehexamine, tetraethylenepentamine, propylene amines such as bis(2-aminopropyl)-amine, cyclic polyamines such as 1,4,7-triazacyclononane, 1,4,7,10-tetraazacyclododecane, star shaped polyamines such as N~1~,N~1~-bis(2-aminoethyl)-1,2-ethanediamine, polylysine, and spermines, preferably pentaerythrityl tetraamine.

Additional homo-multifunctional hydrocarbons for Z are oligocarboxylic acids, oligothiols, oligoalkenes, oligoalkynes, and oligoazides.

In a preferred embodiment, X is selected from the group consisting of an amide-, ester-, thioether-, triazol-, urea-, C—C—, or urethane-linkage, preferably a triazol-, amide- or ester-linkage. According to the invention, an amide-linkage is most preferred (being in line with the above preferred oligoamines for use as Z).

In the multimeric agent of the present invention, Pol preferably is a polymer of a molecular weight of <10,000 Da, more preferably <2,000 Da, most preferably <1,000 Da, or, in other words, is within the range of between 150 Da and 10,000 Da. This range is important for the following reasons:

If the molecular weight of Pol is lower than 150 Da, a steric hindrance might occur in particular in a case, in which large biomolecules are coupled to the multimeric agent. Therefore, from the point of view of the invention, it is preferred that the lower range of the molecular weight of Pol is 150 Da.

It is noted that in particular Pol having a molecular weight lower than 2,000 is preferred, since, under a technical aspect, those polymers can be obtained in essentially uniform length, i.e., in "non-dispersed" quality. Those non-dispersed polymers in turn will result in superior characteristics and quality of the final product.

The upper limit of <10,000 Da is recommendable, since the production costs would increase, the reaction time would increase and, most important, the individual biologically active agents bound to the multimeric agent in this case would behave like single molecules. Or in other words, avidity can not be increased so much, if Pol is >10,000.

In a preferred embodiment is Pol polyethylene glycol (PEG). By using PEGylated molecules, the outstanding characteristics of PEG may be utilized, e.g. non-toxicity, as well as the possibility to provide the overall conjugate with a tailored molecular weight, which reduces elimination of the conjugate from the body by not passing the renal filtration barrier.

In a further embodiment, Pol is non-dispersed or low dispersed. Or in other words, this includes molecules with essentially no distribution of molecular weights, i.e., the molecules are not being polydisperse.

A measure for dispersity is the polydispersity index (PDI), which means the distribution of molecular weights in a given polymer sample. As mentioned above, the PDI calculated is the weight average molecular weight divided by the number average molecular weight. It indicates the distribution of individual molecular weights in a batch of polymers. The PDI has a value always greater than 1, but as the polymer chains approach the ideal Gauss distribution (=monodispersity), the PDI approaches 1. In contrast, PEG <2000 may be obtained in non-dispersed quality by isolating PEGs of an accurately defined number of ethylene glycol units, e.g., by displacement chromatography (U.S. Pat. No. 6,245,238).

According to the present invention, n is an integer from 4-20, preferably 4-15, more preferably 4-8. Thus, the lower limit of n is defined as 4. It is assumed that this number is crucial in order to end up with a substantially increased avidity, which may be considerably lower, if a multimer is used, wherein n=2 or 3. On the other hand, the higher n is, the more complicated the process of manufacturing the multimeric agent will be. The costs for the manufacture of a multimeric agent of n>20 will be too high, the reaction rate will be too slow and it is quite unlikely that a substance Z can be achieved in a sufficient uniformity (i.e., not being polydisperse). n may also be in a range of 4-8, 4-7, 4-6 or 4-6. Further it may be 4, 5, 6, 7 or 8.

In a preferred embodiment, each Y is independently selected from a group of compounds, which can be bonded with an amino group, a thiol group, a carboxyl group, a guanidine group, a carbonyl group, a hydroxyl group, a hydrazine group, an alkyne group, a heterocycle, C-nucleophile group, a C-electrophile group, a phosphate or a sulfate, or can form a chelate or a complex with metals, or can enter into a bond with surfaces like plastics, gold, copper, or silicon.

Y fulfills the function of subsequent coupling of the multimeric agent to a biotechnological or synthetic product as well as to natural products and technical products, i.e., the compounds according to the invention preferably contain an activated functionality Y. In the activated form, each Y is preferably independently selected from the group consisting of $(O\text{-alkyl})_2$, $-OSO_2CH_2CF_3$ (tresyl), (O-aryl)-azides, (O-alkyl)-azides, O-alkyne —CO-Q, maleimidyl, $-O-CO$-nitrophenyl or trichlorophenyl, $-S-S$-alkyl, $-S-S$-aryl, $-SO_2$-alkenyl (vinylsulfone), or -halogen (Cl, Br or I), where Q is selected independently from the group consisting of H, O-aryl, O-benzyl, O—N-succinimide, O—N-sulfosuccinimide, O—N-phthalimide, O—N-glutarimide, O—N-tetrahydrophthalimide, N-norbornene-2,3-dicarboximide, hydroxybenzotriazoles and hydroxy-7-azabenzotriazoles. Y is preferably a —CO-Q group. The review by Zalipsky, S., which appeared in Bioconjugate Chem. 1995, 6, 150-165, provides a good overview of possible activations. This review is incorporated herein in its entirety by reference.

The activating functionality enables the compounds according to the invention to be bonded covalently to biologically active compounds, thereby forming highly desirable, stable conjugates. The coupling to the binding molecule preferably is achieved by a suitable group in the active molecule, for example a cysteine residue which has been introduced into the molecule.

It is noted that, in an embodiment, the multimeric agent of the present invention only carries compounds for Y which are equal. An example of this kind of activation is shown below for a tetramer. However, the present invention also provides embodiments, wherein different types of Y activations are used within one multimeric molecule, i.e. different groups Y, which are independently selected from the group indicated above.

The multimeric agent of the present invention for example has the structure depicted below:

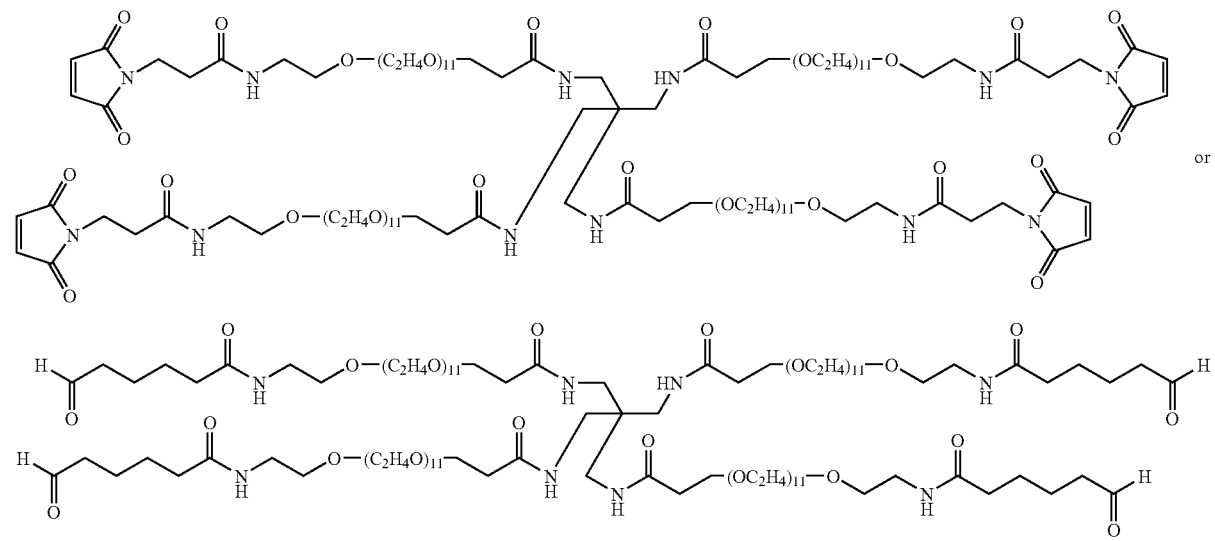

$C_{137}H_{260}N_8O_{60}$
Exact Mass: 2977,75
Mol. Wt.: 2979,55

In a second aspect, the present invention provides a multimeric conjugate, wherein the multimeric agent as explained above is coupled to a biologically active agent via the Y component.

This biologically active agent preferably is independently selected from a peptide, protein, nucleic acid or small molecule having therapeutic or diagnostic relevance. Therefore, in the context of this invention, the conjugate may comprise biologically active agents which are equal, or as an alternative, may comprise one or more different, independently selected biologically active agents.

As an example, the biologically active agent may be selected from growth factors or their receptors like TNF, VEGF, or EGF. In a preferred embodiment, the biologically active agent has an antigen binding activity like antibodies, antibody fragments, antibody like molecules, and scaffold proteins.

The term "binding activity" as used in the context of the present invention means that a molecule has a binding affinity to a specific target molecule.

More precisely, the agent may be a biological receptor, preferably a G protein-coupled receptor (GPCR; e.g., human GLP-1 receptor, human PTH receptor), or EGF receptor, HER2, HER3, VEGF/R1-4, Ep-CAM, or a ligand or a domain thereof, a tumor marker (prostate specific membrane antigen (PSMA)), cytokines (tumor necrosis factor alpha (TNFα), tumor necrosis factor beta (TNFβ)), interleukins (e.g., IL-2, IL-6, IL-11, IL-12), growth factors (e.g., NGF (nerve growth factor) and the pro-form thereof, ProNGF, BMPs, EGF, MIA, MIA-2, FGFs, vascular endothelial growth factor (VEGF), PDGF, PlGF, IGFs), kinases, integrins (e.g., glycoprotein receptor IIb/IIIa (GPIIb/IIIa)), HSA (human serum albumin), F4 fimbrine, T and B cell antigen, preferably CD4, CD11, CD14, CD16, CD20, CD22, CD25, CD34, CD47, CD56, CD83, CD154, CTLA-4, an immunoglobulin or a portion thereof, for example a whole antibody, (e.g., immunoglobulin G, E, M), an Fc portion of, e.g., human immunoglobulin M or a segment of an antibody in the region of the antigen binding site, or a sugar (Lewis Y, Lewis X), or a toxin, for example mycotoxin, or a hormone, for example hydrocortisone.

Further examples are combinations of active agent and a targeting agent, for example, an aminocarboxylic ester, for example a saturated or unsaturated omega-aminocarboxylic ester, a dye, a fluorescence label, an antibiotic, a minor or major groove binder, a biotinyl radical, a streptavidin radical, an intercalating radical, an alkylating radical, a steroid, a lipid, a polyamine, folic acid, a receptor agonist or receptor antagonist, an enzyme inhibitor, a peptide, an antibody or an antibody fragment, an amino sugar, a saccharide or oligosaccharide, e.g., galactose, glucose or mannose, an antisense polymer, a modified surface, a surface-active agent or a complexing agent.

If an antibody is used, this antibody may be selected from a group, which consists of polyclonal antibodies, monoclonal antibodies, humanized antibodies, chimeric antibodies and synthetic antibodies.

The antibody can be additionally linked to a toxic and/or a detectable agent.

The term "antibody", is used herein for intact antibodies as well as antibody fragments, which have a certain ability to selectively bind to an epitope. Such fragments include, without limitations, Fab, F(ab')$_2$ and Fv antibody fragment. The term "epitope" means any antigen determinant of an antigen, to which the paratope of an antibody can bind. Epitope determinants usually consist of chemically active surface groups of molecules (e.g., amino acid or sugar residues) and usually display a three-dimensional structure as well as specific physical properties.

As mentioned above, the production of polyclonal antibodies is commonly known. Detailed protocols can be found for example in Green et al., Production of Polyclonal Antisera, in *Immunochemical Protocols* (Manson, editor), pages 1-5 (Humana Press 1992) and Coligan et al., Production of Polyclonal Antisera in Rabbits, Rats, Mice and Hamsters, in *Current Protocols In Immunology*, section 2.4.1 (1992). In addition, the expert is familiar with several techniques regarding the purification and concentration of polyclonal antibodies, as well as of monoclonal antibodies (Coligan et al., Unit 9, *Current Protocols in Immunology*, Wiley Interscience, 1994).

The production of monoclonal antibodies is commonly known as well. Examples include the hybridoma method (Kohler and Milstein, 1975, Nature, 256:495-497, Coligan et al., section 2.5.1-2.6.7; and Harlow et al., *Antibodies: A Laboratory Manual*, page 726 (Cold Spring Harbor Pub. 1988)), the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96).

A preferred alternative to antibodies or aptamers is a group of proteins having antibody like binding behaviour. Such a protein may preferably be selected from the group consisting of crystallins, spherulins, heat shock proteins, cold shock proteins, β-helix proteins, lipocalins, certins, fibronectins or transcription factors or is GFP, NGF, tendamistat or lysozyme.

In particular, crystallins may serve as binding proteins or as starting proteins for designing novel binding molecules with a predominant beta-sheet structure such as, in particular, gamma-crystallin, a structural protein of the eye lens. Preferably the crystalline is derived from vertebrates, rodents, birds or fish, and is more preferably selected from alpha-, beta- or gamma-crystallin, most preferably it is a gamma-II-crystallin protein.

In this connection, it is referred to the disclosure of U.S. Ser. No. 10/030,605, which is incorporated herein by reference.

A further alternative to antibodies or aptamers may be binding molecules selected from the group consisting of proteins of the protein superfamily of "ubiquitin-like proteins", in particular those having an ubiquitin-like folding motif as well as fragments or fusion proteins thereof each having the ubiquitin-like folding motif. WO 2004/106368 relates to modified proteins of this superfamily of "ubiquitin-like proteins", proteins that have an ubiquitin-like fold. As a result of said modification, the proteins have a binding affinity with respect to a predetermined binding partner that did not exist previously. The contents of WO 2004/106368 are also incorporated herein by reference.

For both groups of binding proteins it is valid that the binding protein due to modifications of those amino acids forming a contiguous region on the surface of the protein, in at least one surface-exposed region of the protein preferably has a binding affinity with respect to a predetermined binding partner that did not exist previously while the original folding motif is maintained.

In a still further embodiment, the overall size of the conjugate of the present invention is such that a renal elimination of the molecule is significantly decelerated. This can be achieved by providing a conjugate having an overall molecular weight of >50,000 Da. Therefore, by using a conjugate of that size, a long-circulating compound can be provided having long-term activity. A conjugate of this type preferably is used for the treatment of chronic conditions in a patient.

As an alternative embodiment, the overall size may be set to less than 50,000 Da in order to provide a conjugate which provides a comparably short term of activity, thus being in particular suitable for the treatment of acute conditions.

The multimeric conjugate of the present invention preferably exhibits an increased avidity compared to the unmodified biologically active agent from which it is derived. As mentioned above, the avidity of the monomeric molecule can be enhanced about 30 fold in using the conjugate structure of the present invention.

In a third aspect, the present invention provides a pharmaceutical or diagnostic composition containing a multimeric conjugate of one or more of the preceding claims and one or more auxiliary agents and/or diluents.

For the proteins modified and selected according to the invention, thus, a broad spectrum of possible applications is available. They can be used not only in the medical-pharmaceutical field but also in the field of analytics, of the nutrient and food stuff industry, of nutrient supplements, of cosmetics, of medical and non-medical diagnostics and analysis etc. Naturally, the field of use depends on the type of binding partner selected.

In the field of human and veterinary medical therapy and prophylaxis pharmaceutically effective medicaments can be prepared by methods known per se. Depending on the galenic preparation these compositions can be administered intravenously, intraperitoneally, intramuscularly, subcutaneously, transdermally or by other methods of application. The type of pharmaceutical preparation depends on the type of disease to be treated, the severity of the disease, the patient to be treated and other factors known to those skilled in the art of medicine. The administration can either be parentally by injection or infusion, by inhalation or by other methods conventionally employed.

The compositions are adapted to contain a therapeutically effective dose. The quantity of the dose to be administered depends on the organism to be treated, the type of disease, the age and weight of the patient and further factors known per se.

The compositions can contain auxiliary agents known per se. These include for example stabilizing agents, surface-active agents, salts, buffers, coloring agents etc.

The pharmaceutical composition can be in the form of a liquid preparation, a cream, a lotion for topical or transdermal application, an aerosol, in the form of powders, in the form of an emulsion or a liposomal preparation. The compositions are preferably sterile, non-pyrogenic and isotonic and contain the pharmaceutically conventional and acceptable additives known per se. Additionally, reference is made to the regulations of the U.S. pharmacopoeia.

In a fourth aspect, the present invention provides a method of producing a multimeric agent as defined hereinabove by reacting a homo-multifunctional agent Z with a homo- or heterofunctional polymer X-Pol-Y in order to form stable linkages and to obtain Z—(X-Pol-Y)$_n$.

It is noted that this reaction may be performed by simply polymerizing X-Pol-Y to Z, or, as an alternative, by convergent synthesis as it will be outlined in the following.

A convergent synthesis is a strategy that aims to improve the efficiency of a multi-step chemical synthesis. In a linear synthesis, the overall yield quickly drops with each reaction step: A→B→C→D. In a convergent synthesis the reaction scheme might be as follows: A→B; C D; B+D→E results in a much higher overall yield. The convergent reaction in particular has advantages in the field of the synthesis of complex molecules and, thus, may in particular be used in the present method.

In a still further aspect, the present invention is directed to a method of producing a multimeric conjugate as defined above, comprising the steps of:
  solubilizing both a biologically active agent and a multimeric agent as defined above in a suitable solvent;
  reacting the multimeric agent Z—(X-Pol-Y)$_n$ as defined herein with said biologically active agent in the same solution; and
  purifying the multimeric conjugate to an essentially homogenous preparation.

The solvent used in this method preferably is capable of solving both the biologically active agent and the multimeric agent. The solvent might be selected from but is not limited to polar or non-polar solvents, for example from organic solvents such as DMF, DMSO, alcohols, dichloromethane, chloroform, THF, DMA, ethyl acetate or aqueous buffer systems such as borate, carbonate, tris, phosphate, acetate, citrate, or formiate buffer.

In the first step of the method, the biologically active agent preferably is solubilized in a concentration from 0.1 to 25 mg/ml, preferably from 1 to 10 mg/ml, in the solvent. The solvent has a pH between 3 and 12, preferably between 4 and 10, more preferably between 5 and 9 and has an overall concentration of buffer salt of less than 250 mM, preferably between 10 and 150 mM, more preferably between 50 and 100 mM. It may further contain additives such as salts, stabilizing, denaturing, and reducing or oxidizing agents.

Preferably, the multimeric agent Z—(X-Pol-Y)$_n$ is added to the solution of the biologically active agent in a molar ratio of 1:n or less as referred to the molar amount of the biologically active agent to be multimerized.

The reaction solution in step 2 is continuously homogenized, e.g., by appropriate stirring or shaking, and maintained at temperatures between −20° C. and 50° C., preferably 0° C. and 37° C., more preferably 4° C. and 25° C.

In the final step of the method, the multimeric conjugate is purified to an essentially homogenous preparation of >90% by weight, more preferably >95% by weight of purity, and, preferably, the purification is done by a chromatographic process, precipitation, or size exclusion such as dialysis or cross-flow filtration.

A still further aspect provides a multimeric agent and a multimeric conjugate obtainable by the above methods.

The multimeric conjugate of the present invention may be used for the diagnosis, prophylaxis and treatment of diseases in which the corresponding binding partner is directly or indirectly involved.

The following, examples are provided for further illustration of the invention. The invention, however, is not limited thereto, and the following Examples merely show the practicability of the invention on the basis of the above description. For a complete disclosure of the invention reference is made also to the literature cited in the application and in the annex which are incorporated in their entirety into the application by reference.

The present invention is further illustrated by the subsequent examples and figures. The figures are showing the following:

FIG. 1: Concentration dependent ELISA of the binding of monomeric AFFILIN® artificial binding protein 8A7 to its target human TNFα (circles). The binding to BSA is plotted as a control (squares).

Figure 2:
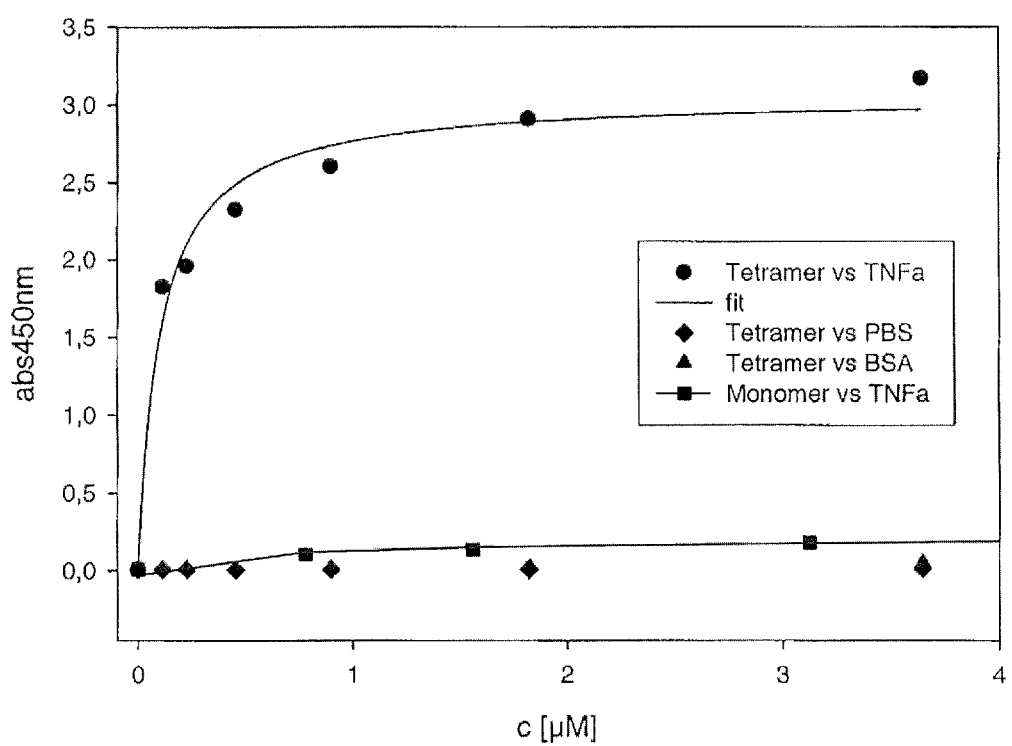

FIG. 2: Concentration dependent ELISA of the binding of monomeric (squares) and tetrameric AFFILIN® artificial binding protein 8A7 (circles) to human TNFα. The binding to BSA (triangles) and the microtiter plate is plotted as a control (diamonds).

Figure 3:
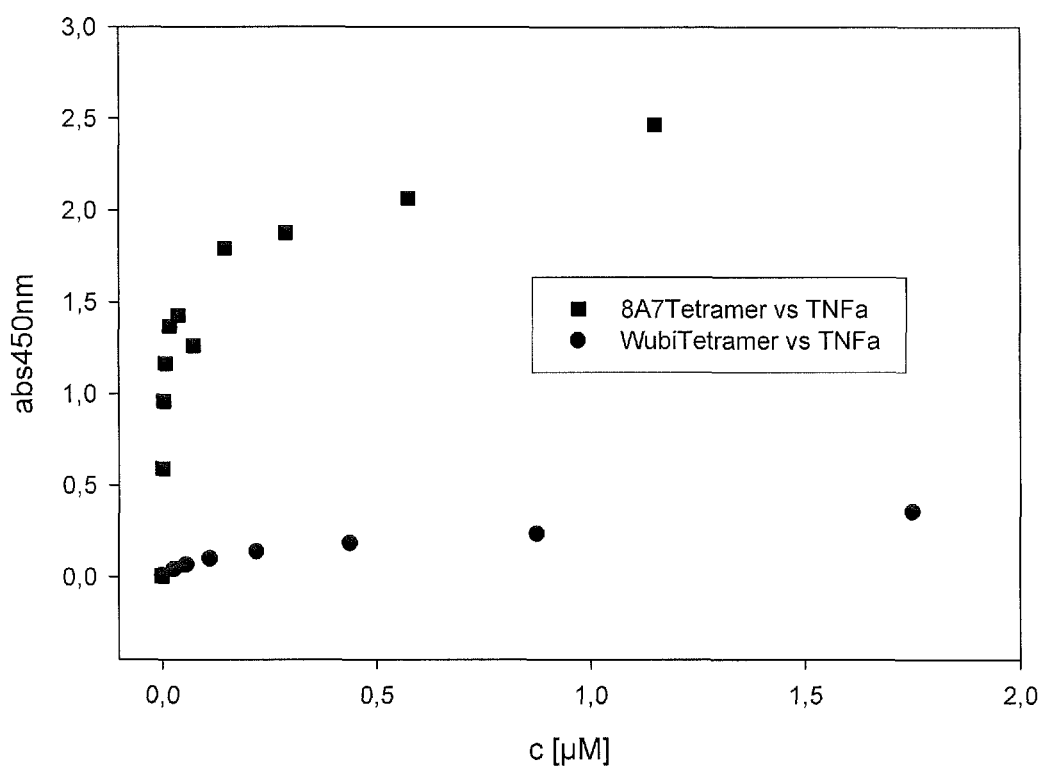

FIG. 3: Concentration dependent ELISA of the binding of tetrameric AFFILIN® artificial binding protein 8A7 (squares) and tetrameric ubiquitin wildtype (circles) to human TNFα.

Figure 4:
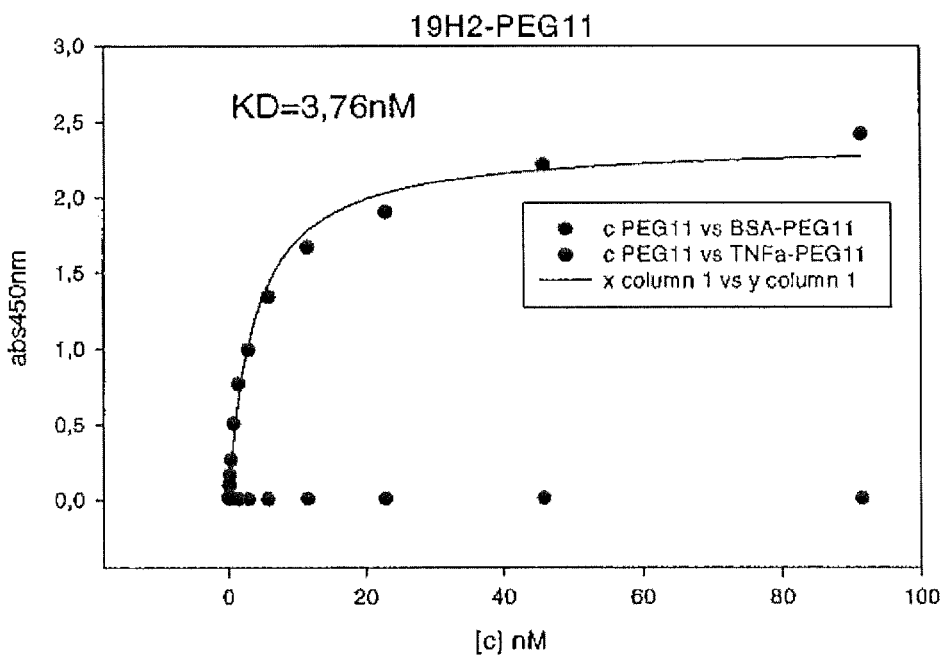
Figure 4:
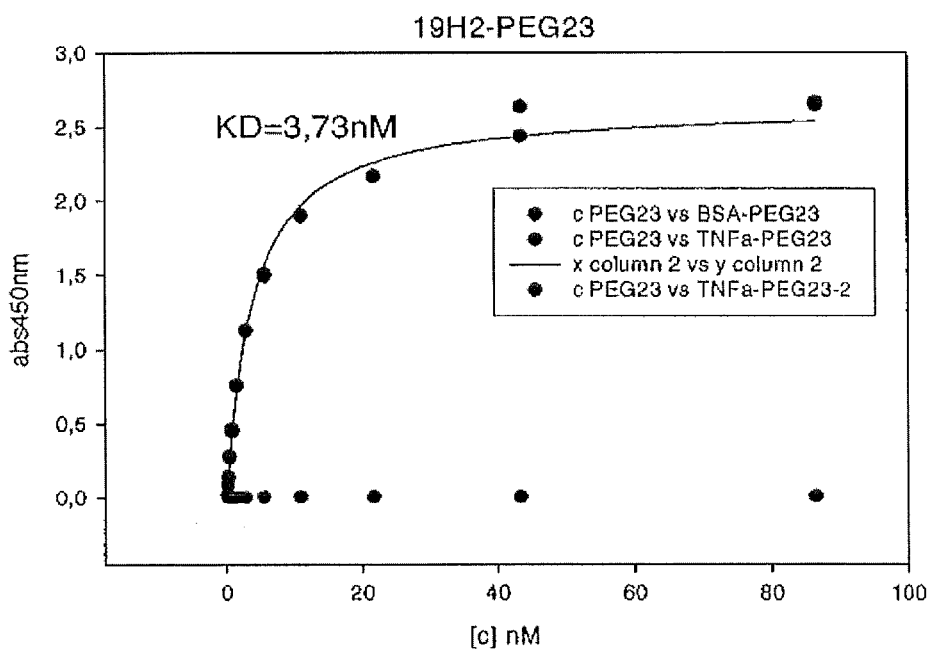

FIG. 4: Concentration dependent ELISA of the binding of tetrameric 19H2 AFFILIN® artificial binding protein towards TNFα. The construct containing 11 PEG units within one arm of the tetramer (A) shows an identical KD value as it was detected for the tetramer with 23 PEG units.

Figure 5:
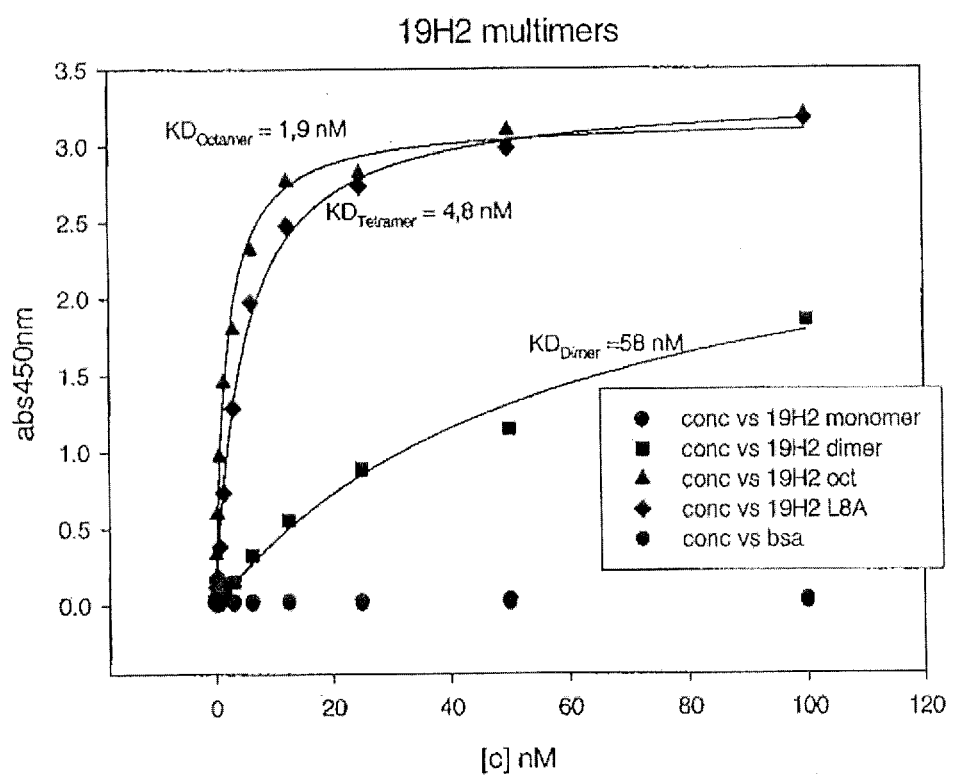

FIG. 5: Concentration dependent ELISA of the binding of octameric 191-12 AFFILIN® artificial binding protein towards TNFα. The Kd value increases with from monomer to dimer, tetramer and octamer.

EXAMPLES

Examples of Multimerizing Agents According to the Invention

Independently from the final structure and activation of the multimerizing agent, the general synthesis strategy is convergent and as follows: Starting with a central homo- or heterofunctional branching/core unit Z, homo- or heterofunctional PEG Pot are reacted with the proximal ends of the core unit applying efficient coupling chemistries. In a second step, the proximal ends of the PEG moiety are activated to result in the group Y. In preferred embodiments, the homo- or heterofunctional PEG Pol used in reaction step one already has a reactive functional group Y or a protected reactive functional group Y* at one proximal end. In the following, general procedures are described starting with polyamines but introducing different reactive groups Y. These general reactions may easily be transferred to multimerizing agents basing on Z that are not oligoamines.

According to the invention, an oligoamine may be used as core structure which is reacted with heterobifunctional or homobifunctional PEGs to form the multimerizing agent. The pentaerythrityl tetraamine core structures can be synthesized as described by Hayes et al. (*Tetrahedron* 2003, 59, 7983-7996). Alternate oligoamines may be selected from the group of Spermines, oligoethyleneamines e.g. diethylenetriamine or oligopropyleneamines e.g. Bis(2-aminopropyl)-amine. Furthermore the oligoamine can be also a member of heterocyclic oligoamines e.g. cyclen. The PEG unit which is used as spacer in the multimerizing agent as well as in terms of PEGylation agent is in the most cases commercially available, otherwise the PEG unit can be synthesized starting from key materials which are polyethylene glycol or derivatives thereof. The synthesis of such PEG units is well known to a chemist.

Due to its high yields amidation reaction has been known for a long time in peptide chemistry. Thus, in preferred embodiments, the amine core and the PEG-unit will be coupled in an amidation step. The PEG-unit is activated at the proximal end with activating functional groups Y. Basically, there is no limitation for Y, many examples are well known in the field of modification of biopharmaceuticals and have been published elsewhere.

Introducing Aldehyde Functions

An aldehyde functional group may be used for the conjugation of biological agents by reductive amination and reversible Schiff base formation, respectively. Different ways are available for introduction of aldehydes. Most preferably, commercially available heterobifunctional PEG are used as key starting materials.

After reacting these PEG with the central core unit Z, the aldehyde functional group is introduced by direct oxidation of the hydroxyl terminus of a PEG-chain by using specific oxidation methods such as the Swern, or Pfitzner-Moffat oxidation (methods based on the activated DMSO) or the TEMPO-oxidation. For stability reasons it is most favourable to use aldehydes with relatively long carbon chains between the aldehyde function and the proximal end of the PEG unit. These aldehydes for example may be derivatives of the propionaldehyde, butyraldehyde, or aldo-carboxylic acids (e.g., 6-aldo heptanoic acid). In further embodiments, the hydroxyl terminus of the PEG chain is alkylated with a halogen or sulfonate derivative of an acetal protected aldehyde (U.S. Pat. No. 5,990,237, U.S. Pat. No. 5,252,714). Another approach is the introduction of an omega-aldo carboxylic acid derivative via an amidation reaction with an amino-PEG derivative.

Alternatively, the aldehyde function may be directly introduced by reacting an oligoamine with a NHS activated PEG-aldehyde derivative. In this case the aldehyde function may be unprotected or acetal protected. An acetal protecting group may either be removed by acid catalysis to form the oligoaldehyde or by in-situ cleavage during reductive amination which proceeds under slightly acidic conditions.

Introducing Azide Functions

An azide functional group may easily be introduced by reacting e.g. an oligoamine with a NHS activated PEG-azide derivative. Such an azide derivative of a PEG can be prepared by converting the hydroxyl function of a HO-PEG-acid to the corresponding azide. Such methods are well known to a chemist.

General Procedure for the Formation of Multimerizing Agents which are Activated as Maleimides:

To a solution of MAL-PEG-NHS (5.4 mmol) in dichloromethane (90 mL) a solution of the oligoamine (1.4 mmol, 500 mg/ml) in DMSO (c=500 mg/mL) and Triethylamine (100 µL) is added. The reaction mixture is afterwards stirred for 48 hours at 20-25° C. Subsequent to the stirring procedure the reaction mixture is diluted with a mixture of dichloromethane/water (50 mL/50 mL). Afterwards the organic phase is separated and the solvent is removed in vacuo. Purification by column chromatography gives the final product as colourless, thick oil or a white solid (yield: 50-80%).

General Procedure for the Formation of Multimerizing Agents which are Activated as Aldehydes (see Example 5):

Oligoolformation:

To a solution of the heterobifunctional HO-PEG-NHS (2.21 mmol) in dichloromethane (20 mL) a solution of the oligoamine (1 mL; 0.55 mmol) in DMSO (c=75 mg/mL) is added. The reaction mixture is afterwards stirred for 12 hours at 20-25° C. Subsequent to the stirring procedure the solvent is removed under reduced pressure. Purification by column chromatography gives the final product (Example 4) as colourless, thick oil (yield: 50%).

Oxidation:

To a mixture of dry dichloromethane (30 mL) and DMSO (500 µL) at −78° C. (dry ice bath) a solution of Oxalyl Chloride (1.1 mL; 2 M in Dichlormethane, 2 mmol; 5.5 eq.) is added within 10 min. The reaction mixture is stirred for additional 15 min at −78° C. Subsequently, a solution of the Oligool (Example 4, 0.37 mmol) in dichloromethane (8 mL) is added at −78° C. within 15 min. After additional stirring for 40 min at −78° C. Triethylamine (700 µL) is added.

The reaction mixture is stirred for additional 2 hours at −78° C. Afterwards the reaction mixture is heated to 25° C. and the solvent is removed in vacuo. Purification by column chromatography gives the final product (Example 5) as colourless, thick oil (yield: 50%).

Example 1
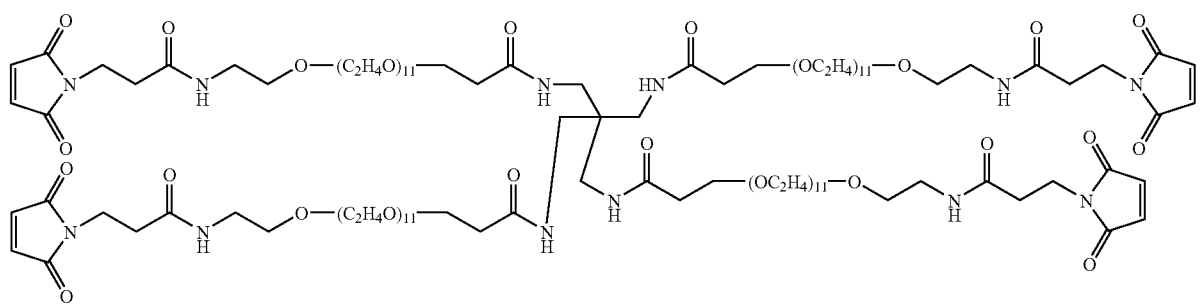
C₁₄₁H₂₄₈N₁₂O₆₄
Exact Mass: 3133.65
Mol. Wt.: 3135.52
MALDI-MS: m/z: 3134.6 [M+H]$^+$; 3156.8 [M+Na]$^+$; 3172.8 [M+K]$^+$.
$^1$H-NMR (400 MHz, CDCl$_3$): δ=2.42-2.52 (16H); 2.93 (8H); 3.37-3.41 (8H); 3.48-3.54 (8H); 3.55-3.69 (176H); 3.71-3.77 (8H); 3.79-3.84 (8H); 6.48 (4H); 6.67 (8H); 7.63-7.67 (4H).
$^{13}$C-NMR (100.6 MHz, CDCl$_3$): δ=34.42; 34.58; 37.41; 38.61; 39.31; 45.41; 67.25; 69.77; 70.24; 70.34; 70.56; 70.62 (OCH$_2$ signals); 134.29; 169.87; 170.57; 172.82.
Example 2
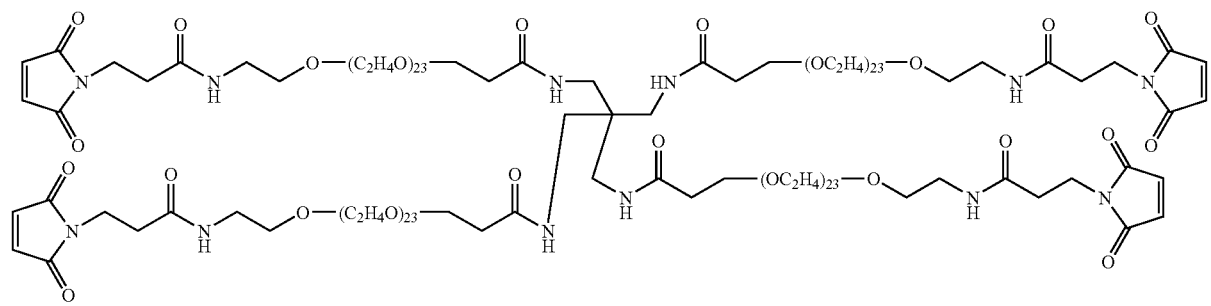
C₂₃₇H₄₄₀N₁₂O₁₁₂
Exact Mass: 5246.91
Mol. Wt.: 5250.04
MALDI-MS: m/z: 5269.79 [M+Na]$^+$.
$^1$H-NMR (400 MHz, CDCl$_3$): δ=2.42-2.52 (16H); 2.82 (8H); 3.37-3.41 (8H); 3.48-3.54 (8H); 3.55-3.64 (368H); 3.71-3.75 (8H); 3.79-3.83 (8H); 6.58 (4H); 6.68 (8H); 7.63-7.67 (4H).
$^{13}$C-NMR (100.6 MHz, CDCl$_3$): δ=34.44; 34.59; 37.42; 38.64; 39.31; 45.42; 67.27; 69.82; 70.23; 70.35; 70.63 (OCH$_2$-signals); 134.29; 169.89; 170.58; 172.82.

Example 3
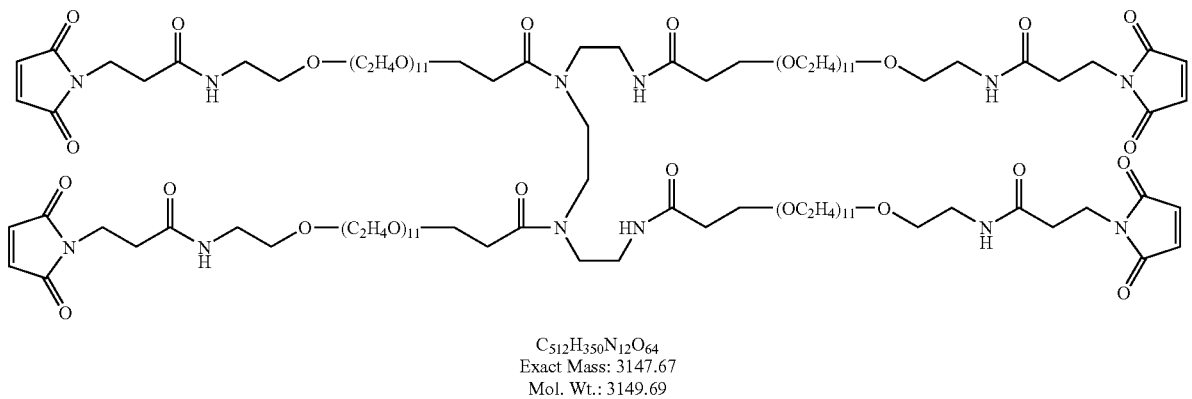
MALDI-MS: m/z: 3170.69 [M+Na]+.
Example 4
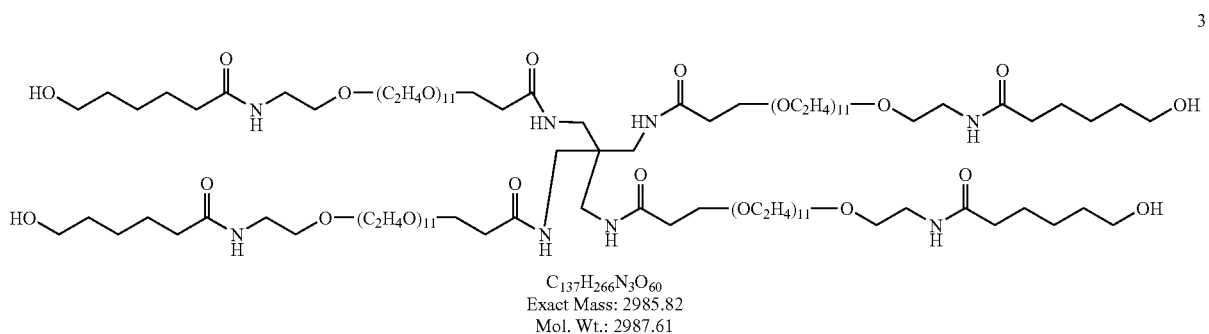
MALDI-MS: m/z: 2986.84 [M+H]+; 3008.84 [M+Na]+; 3024.81 [M+K]+.
Example 5
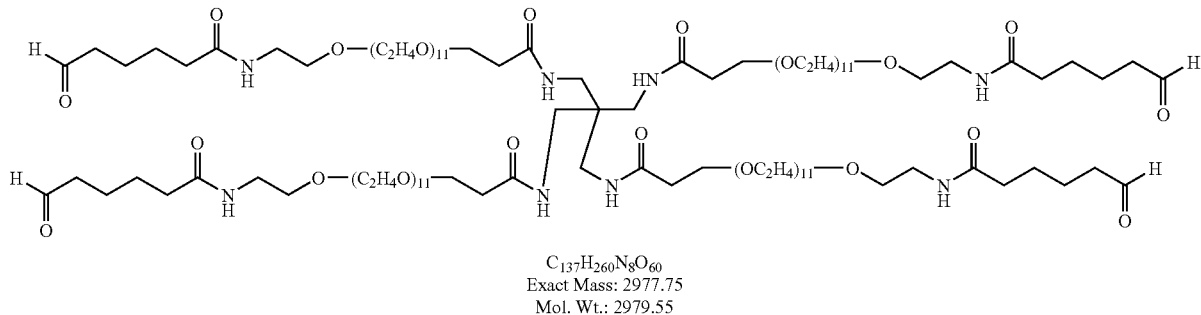
MALDI-MS: m/z: 2978.74 [M+H]+; 3000.75 [M+Na]+; 3016.71 [M+K]+.
$^{1}$H-NMR (300 MHz, CDCl$_3$): δ=1.63-1.66 (16H); 2.17-2.22 (8H); 2.41-2.52 (16H); 2.79-2.83 (8H); 3.40-3.48 (8H); 3.50-3.55 (8H); 3.56-3.68 (176H); 3.70-3.76 (8H); 6.50 (4H); 7.65 (4H); 9.73 (4H).
$^{13}$C-NMR (75.4 MHz, CDCl$_3$): δ=21.69; 25.16; 36.06; 37.41; 39.35; 41.03; 43.68; 45.41; 67.26; 69.91; 69.96; 70.26; 70.34; 70.62; 172.82; 202.38.

Example 6

Azide

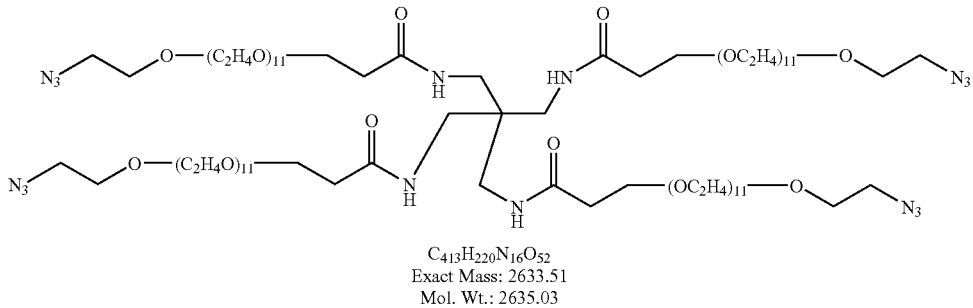

C₄₁₃H₂₂₀N₁₆O₅₂
Exact Mass: 2633.51
Mol. Wt.: 2635.03

Example 7

Alkyne

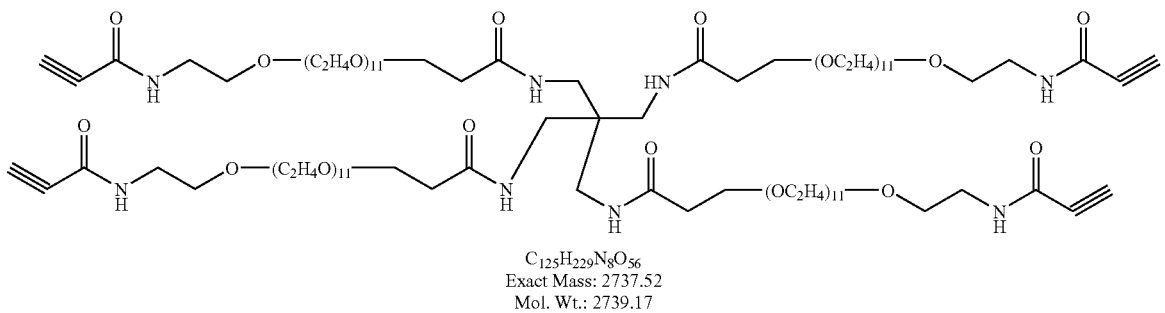

C₁₂₅H₂₂₉N₈O₅₆
Exact Mass: 2737.52
Mol. Wt.: 2739.17

Example 8 pNPC-Ester

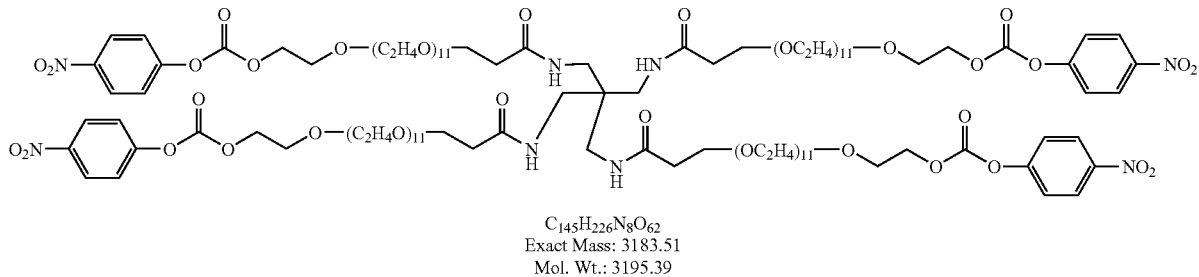

C₁₄₅H₂₂₆N₈O₆₂
Exact Mass: 3183.51
Mol. Wt.: 3195.39

Embodiment with AFFILIN® Artificial Binding Protein 8A7:

Using multimeric tools described in the present invention a tetramer of ubiquitin based AFFILIN® artificial binding protein molecule has been made. The AFFILIN® artificial binding protein 8A7 with affinity towards human TNFα was selected from a combinatorial ubiquitin library according to the patent WO 2004/106368. After 3 rounds of affinity enrichment by phage display the variant 8A7 represents a consensus sequence within the artificial binding site. The variant was therefore chosen for further characterisation and after expression and purification the binding to the predefined target human TNFα was measured by ELISA. FIG. 1 shows the concentration dependent specific binding signal of the 8A7 monomer to TNFα. A weak but specific interaction was detectable with an apparent dissociation constant (KD) of 3 µM.

In order to test if the ubiquitin scaffold itself or the mutimeric agent has an unspecific affinity to TNFα a ubiquitin tetramer was generated as a control. To ensure a specific coupling of a maleimide activated tetrameric PEG-molecule to 8A7 and wild type ubiquitin the surface exposed side chain serine 57 was substituted at DNA level to cysteine using an overlapping extension ligation: First PCR contained 10 µl Pwo buffer (10×, Roche), 2 µl dNTPs (10 mM, Roche), 1 µl F1 primer (100 µM), 1 µl SPWS57Crev primer (100 µM), 1 µl template (8A7 or ubiquitin in pET20b+, 1:5 dilution), 1 µl Pwo polymerase (250 U, Roche) and 84 µl RNAse free water. Second PCR: 10 µl Pwo buffer (10×, Roche), 2 µl dNTPs (10 mM, Roche), 1 µl SPWS57Cfw primer (100 µM), 1 µl pET-20b(+)rev_help primer (100 µM), 1 µl template (8A7 or ubiquitin in pET20b+, 1:5 dilution), 1 µl Pwo polymerase (250 U, Roche) and 84 µl RNAse free water. Both PCRs were run using the following protocol: Denaturation for 1 min 94° C. followed by 25 cycles of denaturation (94° C., 30 sec), annealing (65° C., 45 sec) and elongation (72° C., 40 sec). After 25 cycles a final elongation step was carried for 5 min (72° C.). The resulting PCR fragments were purified using a PCR purification kit (Qiagen, Hilden, Germany). Both fragments were used in a final PCR containing: 10 µl Pwo buffer (10×, Roche), 2 µl dNTPs (10 mM, Roche), 1 µl F1 primer (100 µM), 1 µl WUBIFlagXholrev primer (100 µM), 2 µl template from PCR 1, 2 µl template from PCR 2, 1 µl Pwo polymerase (250 U, Roche) and 81 µl RNAse free water. This PCR was run using the PCR program already described above. After PCR the product was purified using a PCR purification kit (Qiagen) and digested with XbaI and XhoI. Digestion was done as follows: 8 µl of PCR fragment (third PCR), 1 µl XhoI (Promega), 1 µl XbaI (Promega), 2 µl BSA (10×, Promega), 2 µl buffer H (Roche) and 6 µl RNAse free water. The mixture was incubated at 37° C. for 3 hours. pET-20b(+) vector (Novagen) was also digested with XbaI/XhoI: 2 µl XhoI (Promega), 2 µl XbaI (Promega), 2 µl BSA (10×, Promega), 2 µl buffer H (Roche), 6 µl pET-20b(+) vector and 6 µl RNAse free water. The mixture was also incubated at 37° C. for 3 hours. The digested PCR fragment and vector were purified via gel extraction. The PCR fragment was run using 2% NUSIEVE® agarose gel and the vector was separated using a 0.6% SeaKem agarose gel (both from BMA). Fragments were cut off from the gel and the DNA was extracted using a gel extraction kit (Qiagen). Purified fragments were used in a ligation reaction: 3 µl PCR fragment, 1 µl pET-20b(+) vector (XbaI/XhoI cuffed), 1 µl T4 ligase (Promega), 2 µl T4 ligase buffer (Promega) and 13 µl RNAse free water. The ligation was incubated at 6° C. overnight and then purified using a MinElute clean up kit (Qiagen). Purified vector was used for transforming Nova blue cells via electroporation. After electroporation the cells were plated on LB-agar containing 100 µg/ml ampicillin (LB/Amp) and incubated at 37° C. overnight.

DNA Sequence analysis showed the correct substitution of serine 57 to cysteine (see appendix). For Expression of 8A7 and ubiquitin the clones was cultivated in a 1.5 L shaker flask by diluting a preculture 1:100 with LB/Amp and agitating the culture at 200 rpm and 37° C. up to an optical density at 600 nm ($OD_{600}$) of 0.5. Expression was induced by adding IPTG (final concentration 1 mM). Culturing was continued for 4 hours at 30° C. and 200 rpm. The bacteria cells were harvested by centrifugation at 4° C., 6000×g for 20 min. The cell pellet was suspended in 30 ml of NPI-20 buffer including benzonase and lysozyme. Cells were disrupted by ultrasonication (3×20 sec) on ice. The supernatant containing the soluble proteins was obtained after centrifugation of the suspension at 4° C. and 40,000×g for 30 min. Both proteins fused to 6 histidine residues were purified by affinity chromatography at RT. One column of Ni-Agarose (5 ml, GE Healthcare) was equilibrated with 50 ml of NPI-20 including 5 mM mercaptoethanol (β-ME). The supernatant containing the soluble proteins was applied to the column, followed by a washing step with NPI-20 (β-ME, 50 ml). The bound protein was eluted with a linear gradient to 50% NPI-500 (β-ME) in 100 ml. Fractions were analyzed by SDS-PAGE with respect to their purity. Suitable fractions were pooled and applied to a gel filtration column (Superdex 75, 1.6×60 cm, GE Healthcare) equilibrated with PBS (pH 7.4) including 10 mM DTE at a flow rate of 1 mL/min. Purified protein was pooled and applied to 2×5 ml Hitrap Desalting columns (GE Healthcare) equilibrated with coupling buffer (50 mM phosphate, pH 7.0). Maleimide-activated tetrameric PEG molecule (according to claim 8, example 1) was then added to a molar ratio of protein:PEG to 4:1. The mixture was incubated at 25° C. for 2 hours and the reaction was then stopped by adding p-ME to a final concentration of 100 mM for 30 min at 25° C. After a 1:5 dilution with 50 mM acetate buffer (pH 5.0) the pH value of the mixture was set to 5.0 using acetic acid. Then, the protein was applied to a RESOURCE® S column (1 ml, GE Healthcare). Unreacted monomeric protein and the corresponding tetramer were then eluted using a linear salt gradient from 0 to 1 M NaCl (50 mM acetate buffer, pH 5.0). Purity of the tetramer was proofed by rpHPLC analysis and gel electrophoresis. The correct molecular mass of the tetramer was confirmed using MALDI analysis.

Binding of 8A7 (monomer and tetramer) and tetrameric ubiquitin to human TNFα was assayed by a concentration dependant ELISA. Increasing amounts of purified of either monomer or tetramer were applied to NUNC MEDISORPT™ plates coated with human TNFα, BSA and PBS. Antigen coating with 50 µl (10 µg/ml) per well was performed at 4° C. overnight. After washing the plates with PBS, 0.1% TWEEN® 20 pH 7.4 (PBST) the wells were blocked using blocking solution (PBS pH 7.4; 3% BSA; 0.5% TWEEN® 20) at 37° C. for 2 h. Wells were washed again three times with PBST. Different concentrations of monomeric and tetrameric 8A7 AFFILIN® artificial binding protein and tetrameric ubiquitin protein were then incubated in the wells at RT for 1 h (50 µl volume). After washing the wells with PBST the anti-FLAG POD conjugate (Sigma) was applied in a dilution of 1:2000 in PBST. The plate was washed three times with 300 µl buffer PBST/well. 50 µl TMB substrate solution (KEM-EN-Tec) were added to each well and was incubated for 15 min. The reaction was stopped by adding 50 µM $H_2SO_4$ per well. The ELISA plates were read out using the TECAN SUNRISE™ ELISA Reader. The photometric absorbance measurements were done at 450 nm using 620 nm as a reference wavelength. FIG. 2 shows clearly the specific binding of the tetramer 8A7 to human TNFα with an apparent KD value of 100 nM. In comparison to the monomer the affinity was increased by the factor of 30. No binding of ubiquitin tetramer to TNFα was detectable (FIG. 3).

The sequences used are the following:

F1 primer:

```
                                                (SEQ ID NO: 1)
5' - ggagaccacaacggtttccctctagaaataattttgtttaacttt aagaaggagatatacatatg
```

SPWS57Crev primer:

(SEQ ID NO: 2)
5' - cacaaagagtgcggccatcttccagttgcttgcctgcccagatga gcc

SPWS57Cfw primer:

(SEQ ID NO: 3)
5' - ggaagatggccgcactctttgtgactacaacatc pET20b+rev help primer:

(SEQ ID NO: 4)
5' - gggaagaaagcgaaaggagcgg

WUBIFIagXhoIrev primer:

(SEQ ID NO: 5)
5' - ccattccacctcgagacctttatcatcatcatctttgtaatcgcc gccacgcagacgcagc 8A7 (S57C) DNA Sequence:

(SEQ ID NO: 6)
ATGCGGATCTTTGTGGTTACCCTGACCGGCAAGACCATCACTCTGGAGGT

GGAGCCCAGTGACACCATCGAAAATGTGAAGGCCAAGATCCAAGATAAAG

AAGGCATTCCCCCCGACCAGCAGAGGCTCATCTGGGCAGGCAAGCAACTA

GAAGATGGCCGCACTCTTTGTGACTACAACATCCTGAAGACTGGTCCTCT

GCACCTGGTCCTCCGCCTGAGGGGCGGCGATTACAAAGATGATGATGATA

AAGGTCTCGAGCACCACCACCACCACCACTGATAA

8A7 (S57C) amino acid sequence:

(SEQ ID NO: 7)
MRIFVVTLTGKTITLEVEPSDTIENVKAKIQDKEGIPPDQQRLIWAGKQL

EDGRTLCDYNILKTGPLHLVLRLRGGDYKDDDDKGLEHHHHHH

Ubiquitin (S57C) DNA sequence:

(SEQ ID NO: 8)
ATGCAGATCTTCGTGAAGACCCTGACCGGCAAGACCATCACTCTGGAGGT

GGAGCCCAGTGACACCATCGAAAATGTGAAGGCCAAGATCCAAGATAAAG

AAGGCATTCCCCCCGACCAGCAGAGGCTCATCTGGGCAGGCAAGCAACTG

GAAGATGGCCGCACTCTTTGTGACTACAACATCCAGAAAGAGTCGACCCT

GCACCTGGTCCTCCGCCTGAGGGGCGGCGATTACAAAGATGATGATGATA

AAGGTCTCGAGCACCACCACCACCACCACTGATAA

Ubiquitin (S57C) amino acid sequence:

(SEQ ID NO: 9)
MQIFVKTLTGKTITLEVEPSDTIENVKAKIQDKEGIPPDQQRLIWAGKQL

EDGRTLCDYNIQKESTLHLVLRLRGGDYKDDDDKGLEHHHHHH

Embodiment with AFFILIN® Artificial Binding Protein 19H2:

Another ubiquitin based AFFILIN® artificial binding protein (19H2) was tetramerized using the substance of formula

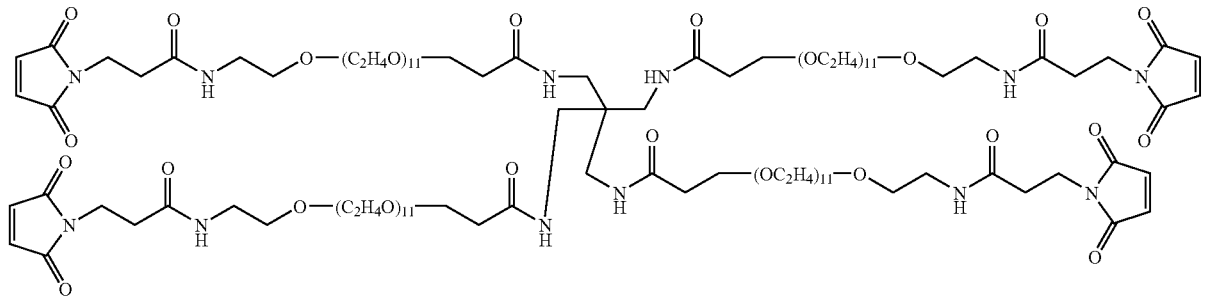

with 11 and 23 PEG units in the linker arm between Z and Y. Expression, purification and coupling as well the purification of the tetramers were done as described for the 8A7 AFFILIN® artificial binding protein (above). ELISA was used to detect the binding of both tetramers (PEG11 and PEG23 linker) towards its target molecule TNFα. FIG. 4 shows that the linker length does not affect the avidity of the tetramers, both show an apparent KD value of 3.7 nM.

The tetramerization of genetically generated dimers (octamerization of monomers) was also performed and tested as well as the dimer alone. For this purpose the 19H2 AFFILIN® artificial binding protein was dimerized using standard PCR techniques. A linker sequence between both 19H2 molecules was also inserted. This linker was a double Gly$_4$Ser standard linker. The second 19H2 molecule within such a homodimer bears a substitution at position 57 (serine to cysteine) for selective coupling of the dimers with the maleimide-activated tetrameric PEG (11) molecule (formula see above). Expression, purification, coupling and binding analysis were done as described above for the monomer. FIG. 5 show the comparison of the binding properties of the monomer, dimer, tetramer and octamer of 191-12 AFFILIN® artificial binding protein towards TNFα. As it can be derived therefrom, the octamer showed the best binding properties.

The invention claimed is:

1. A multimeric agent of the following formula:

Z—(X-Pol-Y)$_n$ wherein:
- Z is a homo-multifunctional hydrocarbon with 1 to 50 carbon atoms which optionally contains heteroatoms;
- X is a hydrocarbon linker with 1-15 carbon atoms, which optionally contains heteroatoms and which is capable of forming a stable linkage between Z and Pol selected from the group consisting of a triazol linkage, an amide linkage, a thioether linkage, a urea linkage, and an ester linkage;
- Pol is a water soluble, linear polymer having a molecular weight of less than 2,000 Daltons,
- Y is a coupling agent capable of coupling to a biologically active agent, and
- n is an integer from 4-20,
- each X-Pol-Y moiety is independently linked to Z via X, such that there are n linkages between Z and Pol,
- and further wherein Z is not a peptidic or amino acid compound.

2. The multimeric agent of claim 1, wherein the homo-multifunctional hydrocarbon is branched.

3. The multimeric agent of claim 1, wherein X is a hydrocarbon linker with 2-10 carbon atoms.

4. The multimeric agent of claim 1, wherein X is a hydrocarbon linker with 3-5 carbon atoms.

5. The multimeric agent of claim 1, wherein n is an integer from 4-15.

6. The multimeric agent of claim 1, wherein n is an integer from 4-8.

7. The multimeric agent of claim 1 or 2, wherein Z is selected from the group consisting of oligoamines, oligocarboxylic acids, oligothiols, oligoalkenes, oligoalkynes, and oligohydrazines.

8. The multimeric agent of claim 1, wherein Pol is a polymer of a molecular weight of <1,000 Da.

9. The multimeric agent of claim 1, wherein Pol is a polymer of a molecular weight of 500-2,000 Da.

10. The multimeric agent of claim 1, wherein Pol is polyethylene glycol (PEG).

11. The multimeric agent of claim 1, wherein Pol is non-dispersed.

12. The multimeric agent of claim 1, wherein each Y independently is selected from a group of compounds which can be bonded with an amino group, a thiol group, a carboxyl group, a guanidine group, a carbonyl group, a hydroxyl group, a hydrazine group, an alkyne group, a heterocycle, C-nucleophile group, a C-electrophile group, a phosphate or a sulfate, or can form a chelate or a complex with metals, or can enter into a bond with surfaces like plastics, gold, copper, or silicon.

13. The multimeric agent of claim 1, wherein the multimeric agent has one of the following structures:

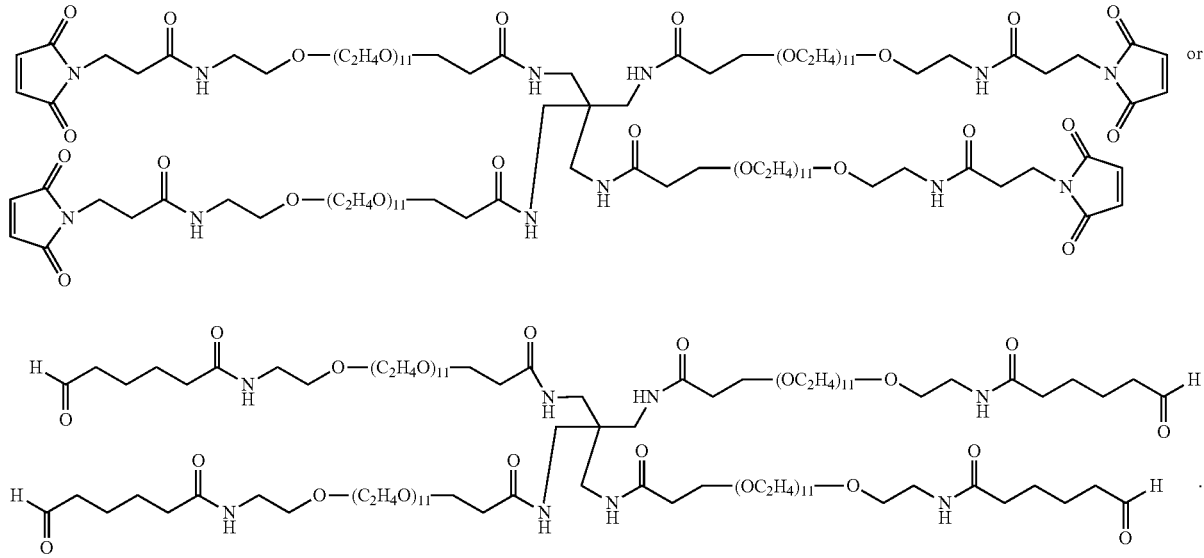

14. A multimeric conjugate comprising the multimeric agent of claim 1 coupled to one or more biologically active agents, each of the one or more biologically active agents being coupled to the multimeric agent of claim 1 via a Y coupling agent.

15. The multimeric conjugate of claim 14, wherein at least one of the biologically active agents is a peptide, a protein, a nucleic acid, or a small molecule having therapeutic or diagnostic relevance.

16. The multimeric conjugate of claim 14, wherein at least one of the biologically active agents is a growth factor or a growth factor receptor.

17. The multimeric conjugate of claim 14, wherein at least one of the biologically active agents has an antigen binding activity.

18. The multimeric conjugate of claim 15, wherein at least one of the biologically active agents is a gamma-crystallin protein.

19. The multimeric conjugate of claim 15, wherein at least one of the biologically active agents is a member of the ubiquitin-like superfamily of proteins having a ubiquitin-like folding motif, or is a fragment or fusion protein thereof having a ubiquitin-like folding motif.

20. The multimeric conjugate of claim 18 or 19, wherein at least one of the biologically active agents is a modified gamma-crystallin protein, a modified ubiquitin-like protein, or a modified fragment or fusion protein of a ubiquitin-like protein comprising one or more modifications of those amino acids forming a contiguous region on the surface of the protein in at least one surface-exposed region of the protein, and further wherein:
   (i) as a result of the one or more modifications, the at least one biologically active agent that has been modified has a binding affinity with respect to a predetermined binding partner that it did not have absent the one or more modifications; and
   (ii) the one or more modifications does not disrupt the ubiquitin-like folding motif.

21. The multimeric conjugate of claim 14, wherein the overall size of the conjugate is greater than 50 000 Da.

22. The multimeric conjugate of claim 14, wherein the conjugate exhibits increased avidity compared to the unmodified biologically active agent from which it is derived.

23. A pharmaceutical or diagnostic composition containing a multimeric conjugate of claim 1 and one or more auxiliary agents and/or diluents.

24. The multimeric conjugate of claim 16, wherein at least one of the biologically active agents is selected from the group consisting of tumor necrosis factor (TNF), vascular endothelial growth factor (VEGF), epidermal growth factor (EGF), and receptors thereof.

25. The multimeric conjugate of claim 17, wherein at least one of the biologically active agents is selected from the group consisting of an antibody, an antibody fragment, an antibody-like molecule, and a scaffold protein.

* * * * *